(12) United States Patent
Romero Ugalde et al.

(10) Patent No.: US 11,883,162 B2
(45) Date of Patent: Jan. 30, 2024

(54) SYSTEM FOR PREDICTING A PATIENT'S BLOOD GLUCOSE LEVEL

(71) Applicant: Commissariat à l'Énergie Atomique et aux Énergies Alternatives, Paris (FR)

(72) Inventors: Hector-Manuel Romero Ugalde, Grenoble (FR); Stéphane Bonnet, Grenoble (FR); Eléonore Maeva Doron, La Tronche Grenoble (FR)

(73) Assignee: Commissariat à l'Énergie Atomique et aux Énergies Alternatives, Paris (FR)

( * ) Notice: Subject to any disclaimer, the term of this patent is extended or adjusted under 35 U.S.C. 154(b) by 302 days.

(21) Appl. No.: 16/982,096

(22) PCT Filed: Mar. 6, 2019

(86) PCT No.: PCT/FR2019/050505
§ 371 (c)(1),
(2) Date: Sep. 18, 2020

(87) PCT Pub. No.: WO2019/180341
PCT Pub. Date: Sep. 26, 2019

(65) Prior Publication Data
US 2021/0100486 A1 Apr. 8, 2021

(30) Foreign Application Priority Data
Mar. 20, 2018 (FR) ........................................ 1852354

(51) Int. Cl.
*A61M 5/172* (2006.01)
*A61B 5/145* (2006.01)
(Continued)

(52) U.S. Cl.
CPC .......... *A61B 5/14532* (2013.01); *A61B 5/024* (2013.01); *A61B 5/1118* (2013.01);
(Continued)

(58) Field of Classification Search
CPC ... A61B 5/14532; A61B 5/024; A61B 5/1118; A61B 5/7275; A61B 5/746; A61M 5/14244; A61M 5/1723; A61M 2005/1726
See application file for complete search history.

(56) References Cited

U.S. PATENT DOCUMENTS

2006/0276771 A1* 12/2006 Galley .................. A61M 5/172
604/503
2007/0060803 A1 3/2007 Liljeryd et al.
(Continued)

OTHER PUBLICATIONS

International Search Report and Written Opinion for International Application No. PCT/FR2019/050505, dated May 16, 2019.
(Continued)

*Primary Examiner* — Alex M Valvis
*Assistant Examiner* — Aurelie H Tu
(74) *Attorney, Agent, or Firm* — Wolf, Greenfield & Sacks, P.C.

(57) ABSTRACT

An automated blood glucose control system, including a processing and control unit capable of predicting, based on a mathematical model, the future trend of the patient's blood glucose G(t), wherein the model takes as inputs: a variable EE(t) representative of the time variation of the patient's energy expenditure; variable IOB(t) representative of the time variation of the patient's quantity of insulin on board; and a variable COB(t) representative of the time variation of the patient's quantity of glucose on board, and wherein the mathematical model is a model of black box type, that is, a non-physiological model only defined by the observation of the effects of input variables EE(t), IOB(t) and COB(t) on
(Continued)

output variable G(t), without taking into account the different known physiological mechanisms operating in the patient's body.

12 Claims, 3 Drawing Sheets

(51) Int. Cl.
*A61B 5/11* (2006.01)
*A61B 5/00* (2006.01)
*A61M 5/142* (2006.01)
*A61B 5/024* (2006.01)

(52) U.S. Cl.
CPC ............ *A61B 5/7275* (2013.01); *A61B 5/746* (2013.01); *A61M 5/14244* (2013.01); *A61M 5/1723* (2013.01); *A61M 2005/1726* (2013.01)

(56) References Cited

U.S. PATENT DOCUMENTS

| | | | |
|---|---|---|---|
| 2012/0078067 A1* | 3/2012 | Kovatchev | G16H 20/17 600/301 |
| 2014/0066890 A1 | 3/2014 | Sloan et al. | |
| 2014/0309615 A1 | 10/2014 | Mazlish | |
| 2016/0193409 A1 | 7/2016 | Facchinetti et al. | |

OTHER PUBLICATIONS

International Preliminary Report on Patentability for International Application No. PCT/FR2019/050505, dated Oct. 1, 2020.
PCT/FR2019/050505, dated Oct. 1, 2020, International Preliminary Report on Patentability.
PCT/FR2019/050505, dated May 16, 2019, International Search Report and Written Opinion.

* cited by examiner

SYSTEM FOR PREDICTING A PATIENT'S BLOOD GLUCOSE LEVEL

This application is a national stage filing under 35 U.S.C. § 371 of International Patent Application Serial No. PCT/FR2019/050505, filed Mar. 6, 2019, which claims priority to French patent application FR18/52354. The contents of these applications are incorporated herein by reference in their entireties.

BACKGROUND

The present disclosure generally concerns the field of blood glucose control, and more particularly aims at a system for predicting the future trend of a patient's blood glucose.

DISCUSSION OF THE RELATED ART

Automated blood glucose regulation systems, also called artificial pancreases, enabling to automatically regulate the insulin inputs of a diabetic patient based on his/her blood glucose history, on his/her meal history, on his/her insulin injection history have already been provided, for example, in French patent application No. 1658881 (B15018/DD16959) filed on Sep. 21, 2016, in French patent application No. 1658882 (B15267/DD17175) filed on Sep. 21, 2016, and in French patent application No. 1756960 (B15860/DD18479) filed on Jul. 21, 2017.

The regulation systems described in the above-mentioned patent applications are MPC-type (model-based predictive control) systems, also called predictive control systems, where the regulation of the administered insulin dose takes into account a prediction of the future trend of the patient's blood glucose, obtained from a model. More particularly, in the systems described in the above-mentioned patent applications, the model used to predict the future trend of the patient's blood glucose is a physiological model describing the assimilation of insulin by the patient's body and its impact on the patient's blood glucose.

More generally, many automated blood glucose control applications use physiological models to predict the future trend of a patient's blood glucose, and implement, taking the prediction into account, actions aiming at maintaining the patient's blood glucose within a desired range.

Known physiological models for predicting the future trend of a patient's blood glucose however have limitations. In particular, in certain conditions, the predictions performed by known physiological models may sometimes not be reliable. This may result in errors in the control or the regulation of the patient's blood glucose, which may cause risks for the patient.

SUMMARY

Thus, an embodiment provides an automated system for controlling a patient's blood glucose, comprising a processing and control unit capable of predicting, based on a first mathematical model, the future trend of the patient's blood glucose $G(t)$ over a prediction period, wherein the first model takes as inputs:
- a variable $EE(t)$ representative of the time variation of the patient's energy expenditure;
- a variable $IOB(t)$ representative of the time variation of the patient's quantity of insulin on board; and
- a variable $COB(t)$ representative of the time variation of the patient's quantity of carbohydrate on board, and wherein the first mathematical model is a model of black box type, that is, a non-physiological model only defined by the observation of the effects of input variables $EE(t)$, $IOB(t)$ and $COB(t)$ on output variable $G(t)$, without taking into account the different known physiological mechanisms operating in the patient's body.

According to an embodiment, the first mathematical model is defined as follows:

$$G(t) = a \cdot y_G + b \cdot u_{EE} + c \cdot u_{IOB} + d \cdot u_{COB},$$

where t is s discretized time variable, $a=[a_1, \ldots, a_{na}]$ is a vector of parameters of dimension $n_a$, $n_a$ being an integer greater than or equal to 1, $b=[b_1, \ldots, b_{nb}]$ is a vector of parameters of dimension $n_b$, $n_b$ being an integer greater than or equal to 1, $c=[c_1, \ldots, c_{nc}]$ is a vector of parameters of dimension $n_c$, $n_c$ being an integer greater than or equal to 1, $d=[d_1, \ldots, d_{nd}]$ is a vector of parameters of dimension $n_d$, $n_d$ being an integer greater than or equal to 1, $y_G=[G(t-1), \ldots, G(t-n_a)]$ is a regression vector of dimension $n_a$, $u_{EE}=[EE(t-n_{k1}), \ldots, EE(t-n_{k1}-n_b)]$ is a regression vector of dimension $n_b$, $n_{k1}$ being an integer greater than or equal to 1, $u_{IOB}=[IOB(t-n_{k2}), \ldots, IOB(t-n_{k2}-n_c)]$ is a regression vector of dimension $n_c$, $n_{k2}$ being an integer greater than or equal to 1, and $u_{COB}=[COB(t-n_{k3}), \ldots, COB(t-n_{k3}-n_d)]$ is a regression vector of dimension $n_d$, $n_{k3}$ being an integer greater than or equal to 1.

According to an embodiment, $n_a$ is in range [1,15], $n_b$ is in range [1,15], $n_c$ is in range [1,15], $n_d$ is in range [1,15], $n_{k1}$ is in range [1,15], $n_{k2}$ is in range [1,15], and $n_{k3}$ is in range [1,15].

According to an embodiment, in operation, the control and processing unit receives a signal $CHO(t)$, representative of the time variation of the quantity of carbohydrates ingested by the patient, and a signal $I(t)$ representative of the time variation of the quantity of insulin injected to the patient.

According to an embodiment, the processing and control unit is configured to calculate the input variables $IOB(t)$ and $COB(t)$ of the first model as follows:

$$IOB(t) = \Sigma_{k=0}^{K} I(t-k) * h_{IOB}(k), \text{ and}$$

$$COB(t) = \Sigma_{k=0}^{K} CHO(t-k) * h_{COB}(k),$$

where K is an integer greater than 1, k is an integer in the range from 0 to K, $h_{IOB}$ is an action function representing the time variation of the effect of the injected insulin on the absorption of blood glucose, and $h_{COB}$ is an action function representing the time variation of the effect of the ingested carbohydrates on the blood glucose.

According to an embodiment, action functions $h_{IOB}$ and $h_{COB}$ are defined as follows:

$$h_{IOB}(t) = \left[1 + \frac{t}{\tau_{IOB}}\right] e^{-\frac{t}{\tau_{IOB}}}, \text{ and}$$

$$h_{COB}(t) = \left[1 + \frac{t}{\tau_{COB}}\right] e^{-\frac{t}{\tau_{COB}}},$$

where $\tau_{IOB}$ and $\tau_{COB}$ are time constants.

According to an embodiment, the system further comprises a device for measuring a physical activity of the patient, the input variable $EE(t)$ of the first model being calculated by the processing and control unit based on the output data $PA(t)$ of the measurement device. According to an embodiment, the measurement device comprises a sensor of the patient's movements.

According to an embodiment, the measurement device further comprises a sensor of the patient's heart rate.

According to an embodiment, the motion sensor delivers a signal $S_{CPM}$ representative of movements performed by the patient, and the heart beat sensor delivers a signal $S_{HR}$ representative of the patient's heart rate, and the input variable EE(t) of the first model is calculated as follows by the processing and control unit:

$$EE(t) = \begin{cases} \alpha_1 * S_{HR}(t) + \beta_1, & S_{HR} \geq S1 \\ \alpha_2 * S_{LC}(t) + \beta_2, & S_{HR} < S1 \text{ et } S_{LC} < S2 \\ \alpha_3 * S_{LC}(t) + \beta_3, & S_{HR} < S1 \text{ et } S_{LC} \geq S2 \end{cases}$$

where signal $S_{LC}$ is a linear combination of signals $S_{HR}$ and $S_{CPM}$, and quantities $\alpha_1$, $\alpha_2$, $\alpha_3$, $\beta_1$, $\beta_2$, $\beta_3$, S1, and S2 are parameters of the system.

According to an embodiment, the processing and control unit is configured to predict, based on the first mathematical model, the future trend of the patient's blood glucose G(t) over a prediction period, to determine whether the blood glucose G(t) predicted by the first model remains or not contained within a desired range, and to trigger an alarm if the blood glucose G(t) predicted by the first model comes out of the desired range.

According to an embodiment, the system further comprises a blood glucose sensor, and an insulin injection device, the processing and control unit is capable of predicting the future trend of the patient's blood glucose based on a second mathematical model and of controlling the insulin injection device by taking the prediction into account, and the processing and control unit being configured to:

a) implement a step of automatic calibration of the second model by taking into account a history of the blood glucose measured by the sensor during a past observation period;

b) at the end of the calibration step, make a first prediction of the future trend of the patient's blood glucose based on the first model and, over the same prediction period, a second prediction of the future trend of the patient's blood glucose based on the second model;

c) calculate at least one numerical indicator representative of the deviation between the first and second predictions; and d) according to the value of the digital indicator, control the insulin injection device by taking into account the second prediction or control the insulin injection device without taking the second prediction into account.

According to an embodiment, the second model is a physiological model comprising a differential equation system describing the time variation of a plurality of state variables.

According to an embodiment, step a) of automatic calibration of the second model comprises a step of estimation of parameters of the differential equation system by minimization of a quantity representative of the error, during a past observation period, between the blood glucose estimated based on the second physiological model and the blood glucose measured by the sensor.

BRIEF DESCRIPTION OF THE DRAWINGS

The foregoing and other features and advantages will be discussed in detail in the following non-limiting description of specific embodiments in connection with the accompanying drawings, in which.

DETAILED DESCRIPTION

Like features have been designated by like references in the various figures. For the sake of clarity, only the elements that are useful for an understanding of the embodiments described herein have been illustrated and described in detail. In particular, the hardware implementation of the processing and control systems has not been detailed, the forming of such a processing and control unit being within the abilities of those skilled in the art based on the functional indications of the present disclosure. The terms "approximately", "substantially", and "in the order of" are used herein to designate a tolerance of plus or minus 10%, preferably of plus or minus 5%, of the value in question.

Figure 1:
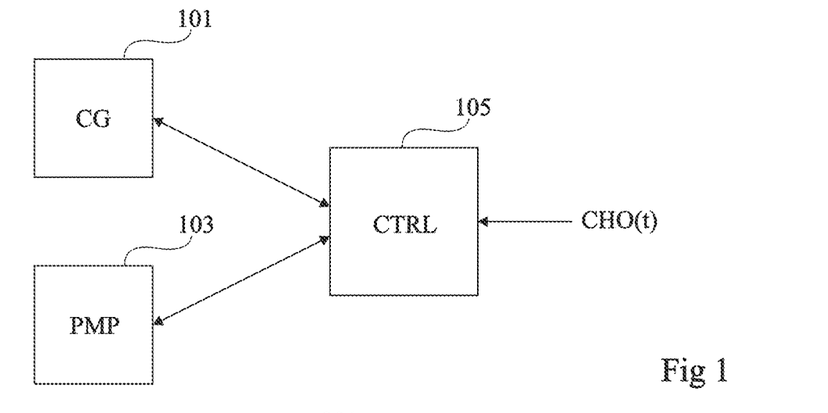
FIG. 1 schematically shows in the form of blocks an example of an automated system for regulating a patient's blood glucose.

FIG. 1 schematically shows in the form of blocks an example of an automated system for regulating a patient's blood glucose described in the above-mentioned French patent applications No. 1658881, No. 1658882, and No. 1756960.

The system of FIG. 1 comprises a sensor 101 (CG) capable of measuring the patient's blood glucose. In normal operation, sensor 101 may be permanently positioned on or inside of the patient's body, for example, at the level of his/her abdomen. Sensor 101 is for example a CGM-type ("Continuous Glucose Monitoring") sensor, that is, a sensor capable of continuously measuring (for example, at least once every five minutes) the patient's blood glucose. Sensor 101 is for example a subcutaneous glucose sensor.

The system of FIG. 1 further comprises an insulin injection device 103 (PMP), for example, a subcutaneous injection device. Device 103 is for example, an automatic injection device of insulin pump type, comprising an insulin reservoir connected to an injection needle implanted under the patient's skin, and the pump may be electrically controlled to automatically inject determined insulin doses at determined times. In normal operation, injection device 103 may be permanently positioned inside of or on the patient's body, for example, at the level of his/her abdomen.

The system of FIG. 1 further comprises a processing and control unit 105 (CTRL) connected on the one hand to blood glucose sensor 101, for example, by a wire link or by a radio (wireless) link, and on the other hand to injection device 103, for example, by wire or radio link. In operation, processing and control unit 105 is capable of receiving the data relative to the patient's blood glucose measured by sensor 101, and of electrically controlling device 103 to inject to the patient determined insulin doses at determined times. In this example, processing and control unit 105 is further capable of receiving, via a user interface, not detailed, data CHO(t) representative of the time variation of the quantity of carbohydrates ingested by the patient.

Processing and control unit 105 is capable of determining the insulin doses to be injected to the patient by taking into account, in particular, the history of the blood glucose measured by sensor 101, the history of the insulin injected by device 103, and the history of carbohydrate ingestion by the patient. To achieve this, processing and control unit 105 comprises a digital calculation circuit (not detailed), for example comprising a microprocessor. Processing and control unit 105 is for example a mobile device carried by the patient all along the day and/or the night, for example, a device of smart phone type configured to implement a regulation method of the type described hereafter.

In the example of FIG. 1, processing and control unit 105 is capable of determining the quantity of insulin to be delivered to the patient by taking into account a prediction of the future trend of his/her blood glucose over time. More particularly, processing and control unit 105 is capable, based on the injected insulin history and on the ingested carbohydrate history, and based on a physiological model describing the assimilation of insulin by the patient's body and its impact on blood glucose, of determining a curve representative of the expected trend of the patient's blood glucose over time, over a period to come called prediction period or prediction horizon, for example, a period from 1 to 10 hours. Taking this curve into account, processing and control unit 105 determines the insulin doses that should be injected to the patient during the prediction period to come, so that the patient's real blood glucose (as opposed to the blood glucose estimated based on the physiological model) remains within acceptable limits, and in particular to limit risks of hyperglycemia or of hypoglycemia. In such an operating mode, as will be explained in further detail hereafter, the data relative to the real blood glucose measured by sensor 101 are mainly used for purposes of calibration of the physiological model.

Figure 2:
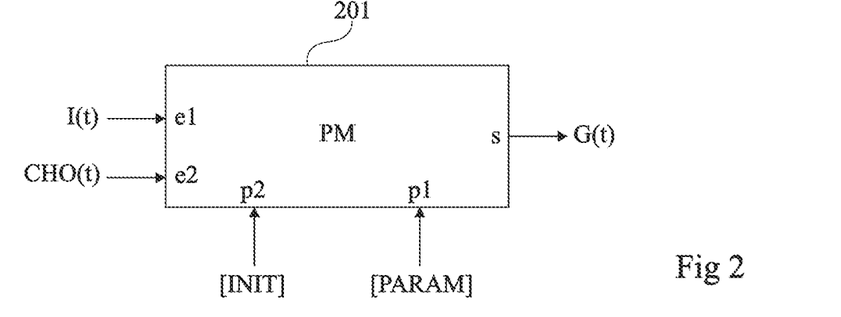
FIG. 2 is a simplified representation of a physiological model used in the system of FIG. 1 to predict the future trend of the patient's blood glucose.

FIG. 2 is a simplified representation of a physiological model 201 (PM) used in the system of FIG. 1 to predict the future trend of the patient's blood glucose. In FIG. 2, the model is shown in the form of a processing block comprising:

- an input e1 having a signal I(t) representative of the variation, over time t, of the quantity of insulin injected to the patient, applied thereto;
- an input e2 having a signal CHO(t) representative of the trend, over time t, of the quantity of carbohydrates ingested by the patient, applied thereto; and
- an output s delivering a signal G(t) representative of the trend, over time t, of the patient's blood glucose.

Physiological model 201 is for example a compartmental model comprising, in addition to input variables I(t) and CHO(t) and output variable G(t), a plurality of state variables corresponding to physiological variables of the patient, varying over time. The time variation of the state variables and of output variable G(t) is ruled by a differential equation system comprising a plurality of parameters represented in FIG. 2 by a vector [PARAM] applied to an input p1 of block 201. The response of the physiological model is further conditioned by the initial states or initial values assigned to the state variables, represented in FIG. 2 by a vector [INIT] applied to an input p2 of block 201.

As an example, the physiological model 201 used in the system of FIG. 1 is the model called Hovorka model, described in the article entitled "Nonlinear model predictive control of glucose concentration in subjects with type 1 diabetes" of Roman Hovorka et al. (Physiol Meas. 2004; 25:905-920), and in the article entitled "Partitioning glucose distribution/transport, disposal, and endogenous production during IVGTT", of Roman Hovorka et al. (Am J Physiol Endocrinol Metab 282: E992-E1007, 2002). More generally, any other physiological model describing the assimilation of insulin by a patient's body and its effect on the patient's blood glucose may be used.

Among the parameters of vector [PARAM], some may be considered as constant for a given patient. Other parameters, called time-dependent parameters hereafter, are however capable of varying over time. Due to this variability of certain parameters of the system, it is in practice necessary to regularly recalibrate the model used, for example, every 1 to 20 minutes, for example, every 5 minutes, to make sure that the predictions of the model remain relevant. Such an update of the model, called model personalization, should be capable of being automatically carried out by the system of FIG. 1, that is, without requiring physically measuring the time-dependent parameters of the system on the patient and then transmitting them to processing and control unit 105.

Figure 3:
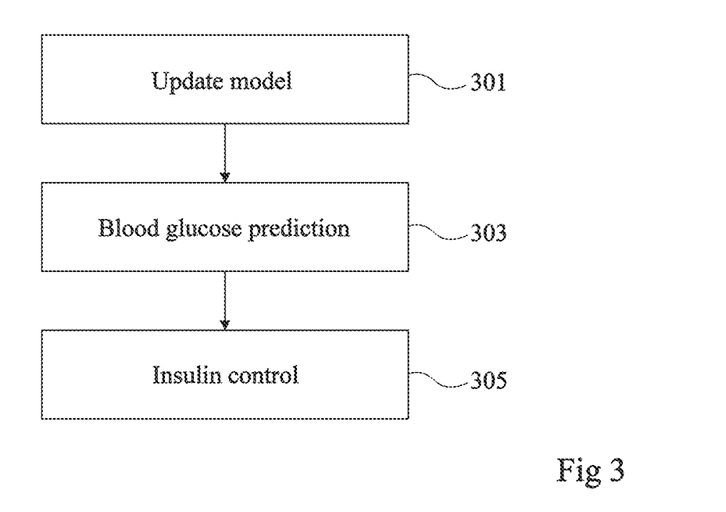
FIG. 3 is a diagram illustrating an example of an automated blood glucose regulation method capable of being implemented by the system of FIG. 1.

FIG. 3 is a diagram illustrating an example of an automated glucose regulation method capable of being implemented by the system of FIG. 1.

This method comprises a step 301 of recalibration or update of the model, which may for example be repeated at regular intervals, for example, every 1 to 20 minutes. During this step, processing and control unit 105 implements a method of re-estimation of the time-dependent parameters of the model, taking into account the data relative to the insulin effectively injected by device 103 and the data relative to the real blood glucose measured by sensor 101 for a past observation period of duration T, for example a period from 1 to 10 hours preceding the calibration step. More particularly, during the calibration step, processing and control unit 105 simulates the patient's behavior over the past observation period based on the physiological model (taking into account possible carbohydrate ingestions and insulin injections during this period) and compares the curve of the blood glucose estimated by the model with the curve of the real blood glucose measured by the sensor during this same period. Processing and control unit 105 then searches, for the time-dependent parameters of the model, a set of values leading to minimizing a quantity representative of the error between the curve of the blood glucose estimated by the model and the curve of the real blood glucose measured by the sensor during the observation period. As an example, the processing and control unit searches for a set of parameters leading to minimizing an indicator m representative of the area or deviation between the curve of the blood glucose estimated by the model and the curve of the real blood glucose measured by the sensor during the observation period, also called standard deviation between the estimated glucose and the real glucose, for example defined as follows:

$$m = \frac{1}{\Delta T} \sum_{t=t_0-\Delta T}^{t_0} |G^r(t) - G(t)|^2 \qquad \text{(eq 1)}$$

where t is a discretized time variable, $t_0-\Delta T$ corresponds to the time of beginning of the past observation phase, $t_0$ corresponds to the end time of the past observation phase (for example corresponding to the time of beginning of the model calibration step), $G^r$ is the curve of time variation of the real blood glucose measured by sensor 101 during period $[t_0-\Delta T, t_0]$, and G is the curve of the blood glucose estimated based on the model during period $[t_0-\Delta T, t_0]$. As a variation, for the calculation of the mean standard deviation, variable $\Delta T$ may be replaced with the number of measurements performed during the past observation period. The optimal parameter search algorithm used during this step is not detailed in the present application, the described embodiments being compatible with usual algorithms used in various field to solve problems of parameter optimization by minimization of a cost function (with or without constraints).

It should be noted that during step 301, in addition to the time-dependent parameters of the model, processing and control unit 105 defines a vector [INIT] of initial states (states at time $t_0-\Delta T$) of the state variables of the model, to be able to simulate the patient's behavior from the model. To define the initial states of the state variables of the model, a first possibility comprises making the assumption that, in the period preceding the observation period $[t_0-\Delta T, t_0]$ having the model calibration based thereon, the patient was in a stationary state, with a constant injected insulin flow, and no dietary intake of carbohydrate. Under this assumption, all the derivatives of the differential equation system may be considered as zero at initial time $t_0-\Delta T$. The values at time $t_0-\Delta T$ of the state variables of the system may then be analytically calculated. To improve the initialization, another possibility comprises making the same assumptions as previously, but adding the constraint that the glucose estimated at time $t_0-\Delta T$ is equal to the real glucose measured by the sensor. To further improve the initialization, another possibility is to consider the initial states of the state variables of the model as random variables, just as the time-dependent parameters of the model. The initial states of the state variables are then determined in the same way as the time-dependent parameters of the model, that is, processing and control unit 105 searches for a set of values of initial states [INIT] resulting in minimizing a quantity representative of the error between the curve of the blood glucose estimated by the model and the curve of the real blood glucose during the past observation period.

The method of FIG. 3 further comprises, after step 301, a step 303 of prediction, by processing and control unit 105, of the time variation of the patient's blood glucose over a prediction period to come $[t0, t_0+T_{pred}]$ of duration $T_{pred}$, for example, in the range from 1 to 10 hours, based on the physiological model updated at step 301 and taking into account the history of the insulin injected to the patient and the history of carbohydrates ingested by the patient.

The method of FIG. 3 further comprises, after step 303, a step 305 of determination, by processing and control unit 105, and taking into account the future blood glucose curve predicted at step 303, of the insulin doses to be injected to the patient for the prediction period to come $[t0, t_0+T_{pred}]$. At the end of this step, processing and control unit 105 may program injection device 103 to deliver the doses determined during the prediction period $[t0, t_0\pm T_{pred}]$.

Steps 303 of prediction of the blood glucose and 305 of determination of the future doses of insulin to be delivered may for example be repeated at each update of the physiological model (that is, after each iteration of step 301), for each new carbohydrate ingestion notified by the patient, and/or for each new administration of an insulin dose by injection device 103.

In a regulation system of the type described in relation with FIGS. 1 to 3, the reliability of the prediction of the future trend of the blood glucose is particularly important to correctly determine the insulin doses to be delivered to the patient, and accordingly to correctly regulate the patient's blood glucose.

More generally, in many automated blood glucose control applications, the prediction of the future trend of the patient's blood glucose plays an important role to enable to maintain the blood glucose within a desired range (for example corresponding to a normoglycemia range).

As previously indicated, known physiological models for predicting the future trend of a patient's blood glucose however have certain limitations. In particular, in certain conditions, the predictions made by the model may sometimes not be reliable. This may result in errors in the control or the regulation of the patient's blood glucose, which may cause risks for the patient.

Thus, it would be desirable to have an automated blood glucose prediction system overcoming all or part of the disadvantages of known blood glucose prediction systems.

According to an aspect of the described embodiments, a system where the prediction of the future trend of the patient's blood glucose is made by taking into account not only the history of the insulin injected to the patient and the history of the carbohydrates ingested by the patient, but also data representative of the patient's physical activity, is provided.

Figure 4:
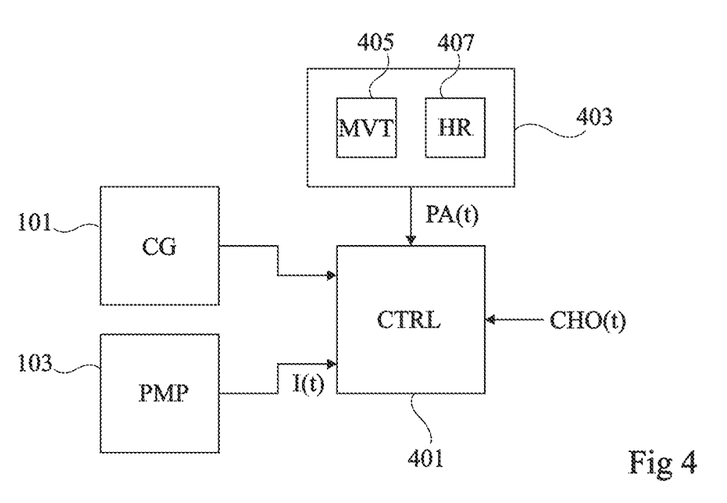
FIG. 4 schematically shows in the form of blocks an embodiment of an automated system for predicting a patient's blood glucose.

FIG. 4 schematically shows in the form of blocks an embodiment of an automated system for predicting a patient's blood glucose.

The system of FIG. 4 comprises a processing and control unit 401 (CTRL). In operation, processing and control unit 401 is capable of receiving data CHO(t) representative of the time variation of the quantity of carbohydrates ingested by the patient, data I(t) representative of the time variation of the quantity of insulin injected to the patient, and data PA(t) representative of the time variation of the patient's physical activity.

The ingested carbohydrate data CHO(t) are for example input by the patient via a user interface, not detailed.

The injected insulin data I(t) may also be input by the patient via a user interface. As a variant, the injected insulin data I(t) are directly communicated to processing and control unit 401 by an insulin injection device. In the example of FIG. 4, the system comprises an insulin injection device 103 (PMP), for example, identical or similar to the device 103 of FIG. 1. Insulin injection device 103 is coupled to processing and control unit 401, for example, by a wire link or a radio link (wireless) and communicates to processing and control unit 401 the injected insulin data I(t). As a variant, processing and control unit 105 is configured to electrically control device 103 to inject to the patient determined insulin doses at determined times. In this case, the injected insulin data I(t) are known by processing and control unit 401 and do not have to be transmitted thereto.

In the example of FIG. 4, the system further comprises a device 403 capable of measuring the patient's physical activity. Device 403 is coupled to processing and control unit 401, for example, by a wire link or a radio link (wireless), and communicates to processing and control unit 401 the patient's physical activity data PA(t). Device 403 is for example a mobile device carried by the patient all along the day and/or the night. As an example, device 403 comprises at least one motion sensor 405 (MVT), for example, an accelerometer. Device 403 may further comprise a sensor 407 (HR) of the patient's heart rate.

The system of FIG. 4 may further comprise a sensor 101 (CG), for example, identical or similar to the sensor 101 of the system of FIG. 1, capable of measuring the patient's blood glucose. Sensor 101 may be coupled, for example, by wire link or by radio link (wireless), to processing and control unit 401. As an example, in operation, processing and control unit 401 is capable of receiving the patient's blood glucose data measured by sensor 101.

In the embodiment of FIG. 4, processing and control unit 401 is capable of predicting the future trend of the patient's blood glucose and, possible, of implementing an action of control or of regulation of the patient's blood glucose to maintain the patient's blood glucose within a desired range. More particularly, processing and control unit 401 is capable, based on the injected insulin history, on the ingested carbohydrate history, and on the history of the patient's physical activity, and based on a mathematical model, of determining a curve representative of the expected trend of the patient's blood glucose over time, over a period to come. To achieve this, processing and control unit 401 comprises a digital calculation circuit (not detailed), for example comprising a microprocessor. Processing and control unit 401 is for example a mobile device carried by the patient all along the day and/or the night, for example, a device of smart phone type configured to implement a method of prediction and/or of control of the patient's blood glucose.

Figure 5:
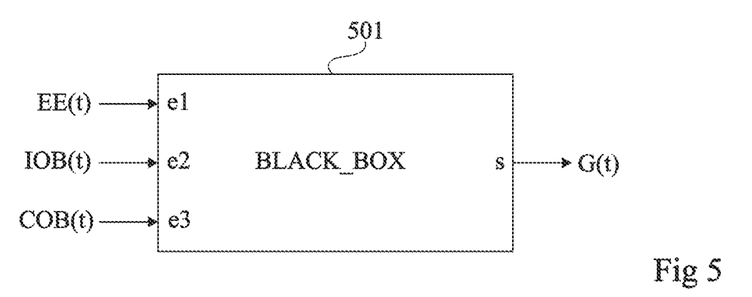
FIG. 5 is a simplified representation of a model used in the system of FIG. 4 to predict the future trend of the patient's blood glucose.

FIG. 5 is a simplified representation of a mathematical model 501 (BLACK_BOX) used in the system of FIG. 4 to predict the future trend of the patient's blood glucose. In FIG. 5, the model is shown in the form of a processing block comprising:

an input e1 having a signal EE(t) representative of the variation, according to time t, of the patient's energy expenditure, that is, of the physical effort made by the patient at time t, applied thereto (as an example, signal EE(t) is representative of the quantity of energy spent at time t by the patient to enable his/her organism to operate properly, to ensure all its physical functions and, possibly, to make a physical effort);

an input e2 having a signal IOB(t) representative of the variation according to time t of the patient's quantity of insulin on board, that is, of the quantity of insulin still active (that is, still capable of having an effect on the blood glucose) at time t in the patient's body, applied thereto;

an input e3 having a signal COB(t) representative of the variation according to time t of the patient's quantity of carbohydrate on board, that is, of the quantity of carbohydrates ingested by the patient still capable, at time t, of having an effect on the patient's blood glucose, applied thereto; and an output s delivering a signal G(t) representative of the trend, over time t, of the patient's blood glucose.

According to an aspect of an embodiment, the model 501 of FIG. 5 is a model of black box type, that is, a non-physiological model, only defined by the observation of the effects of input variables EE(t), IOB(t), and COB(t) on output G(t), without taking into account the different known physiological mechanisms operating in the patient's body and having an effect on the patient's blood glucose. The model 501 of FIG. 5 is for example a model of ARX type, that is, an autoregressive model with external inputs. As an example, model 501 is defined by a single equation, as follows:

$$G(t) = a \cdot y_G + b \cdot u_{EE} + c \cdot u_{IOB} + d \cdot u_{COB} \quad (eq2)$$

where t is a discretized time variable, $a=[a_1, \ldots, a_{na}]$ is a vector of parameters of dimension $n_a$, $n_a$ being an integer greater than or equal to 1 and preferably greater than or equal to 2, $b=[b_1, \ldots, b_{nb}]$ is a vector of parameters of dimension $n_b$, $n_b$ being an integer greater than or equal to 1 and preferably greater than or equal to 2, $c=[c_1, \ldots, c_{nc}]$ is a vector of parameters of dimension $n_c$, $n_c$ being an integer greater than or equal to 1 and preferably greater than or equal to 2, $d=[d_1, \ldots, d_{nd}]$ is a vector of parameters of dimension $n_d$, $n_d$ being an integer greater than or equal to 1 and preferably greater than or equal to 2, $y_G = [G(t-1), \ldots, G(t-n_a)]$ is a regression vector of dimension $n_a$, $u_{EE} = [EE(t-n_{k1}), \ldots, EE(t-n_{k1}-n_b)]$ is a regression vector of dimension $n_b$, $n_{k1}$ being an integer greater than or equal to 1, $u_{IOB} = [IOB(t-n_{k2}), \ldots, IOB(t-n_{k2}-n_c)]$ is a regression vector of dimension $n_c$, $n_{k2}$ being an integer greater than or equal to 1, and $u_{COB} = [COB(t-n_{k3}), \ldots, COB(t-n_{k3}-n_d)]$ is a regression vector of dimension $n_d$, $n_{k3}$ being an integer greater than or equal to 1.

Calling T the sampling period of the system, for each of variables G, EE, IOB, and COB of the model, value G(t), respectively EE(t), respectively IOB(t), respectively COB(t) corresponds to the value of the variable at time t, and value G(t-j), respectively EE(t-j), respectively IOB(t-j), respectively COB(t-j), j being an integer, corresponds to the value of the variable at time t-j*T.

As an example, the sampling period of the system is in the range from 0.5 to 30 minutes, for example, in the order of 10 minutes.

In this example, quantities $n_a$, $n_b$, $n_c$ and $n_d$ are the orders of the model, and quantities $n_{k1}$, $n_{k2}$ and $n_{k3}$ are the delays of the model.

The input variable JOB of the model may be calculated based on the injected insulin data I(t) and based on an action function $h_{IOB}$ representing the time variation of the effect of the injected insulin on the absorption of the blood glucose. As an example, the input variable JOB of the model is defined as follows:

$$IOB(t) = \sum_{k=0}^{K} I(t-k) * h_{IOB}(k) \quad (eq3)$$

where K is an integer greater than 1 and k is an integer in the range from 0 to K.

The input variable COB of the model may be calculated based on the ingested carbohydrate data CHO(t) and on an action function $h_{COB}$ representing the time variation of the effect of the ingested carbohydrates on the glycemia (or blood glucose). As an example, the input variable COB of the model is defined as follows:

$$COB(t) = \sum_{k=0}^{K} CHO(t-k) * h_{COB}(k) \quad (eq4)$$

In the above-mentioned equations eq3 and eq4, quantity K defines the duration d for which the history of injected insulin or of ingested carbohydrates is taken into account for the calculation of input variables IOB(t) and COB(t) of the model, such that d=K*T. As an example, duration d is in the range from 500 to 2,500 minutes, for example in the order of 1,500 minutes, for example, equal to 1,440 minutes.

Action functions $h_{IOB}$ and $h_{COB}$ are for example defined as follows:

$$h_{IOB}(t) = \left[1 + \frac{t}{\tau_{IOB}}\right] e^{-\frac{t}{\tau_{IOB}}} \quad (eq\ 5)$$

-continued $$h_{COB}(t) = \left[1 + \frac{t}{\tau_{COB}}\right] e^{-\frac{t}{\tau_{COB}}} \quad \text{(eq 6)}$$

where $\tau_{IOB}$ is a time constant, for example in the range from 5 to 120 minutes, for example, in the order of 50 minutes, and where Tam is a time constant, for example, different from $\tau_{IOB}$, for example in the range from 5 to 120 minutes, for example, in the order of 40 minutes.

The input variable EE(t) of the model may be calculated from the output signals of the motion sensor 405 and of the heart rate sensor 407 (FIG. 4) of the system. As an example, motion sensor 405 delivers a signal $S_{CPM}$ representative of the patient's movements, for example, representative of a number of movements per minute performed by the patient, for example, representative of the number of steps per minute performed by the patient, and heart rate sensor 407 delivers a signal $S_{HR}$ representative of the patient's heart rate (number of beats per minute). More particularly, in this example, signal $S_{HR}$ is equal to the difference between the patient's heart rate (number of beats per minute) at time t and the patient's heart rate at rest (which may be a constant of the system). Input variable EE(t) can then be calculated as follows:

$$EE(t) = \begin{cases} \alpha_1 * S_{HR}(t) + \beta_1, & S_{HR} \geq S1 \\ \alpha_2 * S_{LC}(t) + \beta_2, & S_{HR} < S1 \text{ et } S_{LC} < S2 \\ \alpha_3 * S_{LC}(t) + \beta_3, & S_{HR} < S1 \text{ et } S_{LC} \geq S2 \end{cases} \quad \text{(eq 7)}$$

where signal $S_{LC}$ is a linear combination of signals $S_{HR}$ and $S_{CPM}$, such that $S_{LC}(t)=\theta 1*S_{CPM}(t)+\theta 2*S_{HR}(t)$, and quantities $\alpha_1$, $\alpha_2$, $\alpha_3$, $\beta_1$, $\beta_2$, $\beta_3$, $\theta 1$, $\theta 2$, S1 and S2 are parameters of the system.

As an example, signals EE(t), IOB(t), and COB(t) may be calculated at a first sampling period, for example, in the order of 1 minute, and then sampled at a higher period T, for example, in the order of 10 minutes.

As an example, value $\alpha_1$ is in the range from 1 to 10, for example, in the order of 5.45, value $\alpha_2$ is in the range from 100 to 500, for example, in the order of 256.1, value $\alpha_3$ is in the range from 10 to 200, for example, in the order of 86, value $\beta_1$ is in the range from −200 to 0, for example, in the order of −66.1, value $\beta_2$ is in the range from −10 to 10, for example, in the order of −0.13, and value $\beta_3$ is in the range from 10 to 200, for example, in the order of 82.4. As an example, threshold S1 is in the range from 20 to 60, for example, in the order of 40, and threshold S2 is in the range from 0.1 to 1, for example, in the order of 0.5. Values $\theta 1$ and $\theta 2$ are for example respectively in the order of 0.000084 and in the order of 0.0086. An example of a method of estimating an individual's energy expenditure, capable of being used to calculate input variable EE(t) of the model, is described in further detail in the article entitled "An original piecewise model for computing energy expenditure from accelerometer and heart rate signals" of H. M. Romero-Ugalde et al. (Physiological Measurement, vol. 38, no. 8, p. 1599, 2017).

Figure 6:
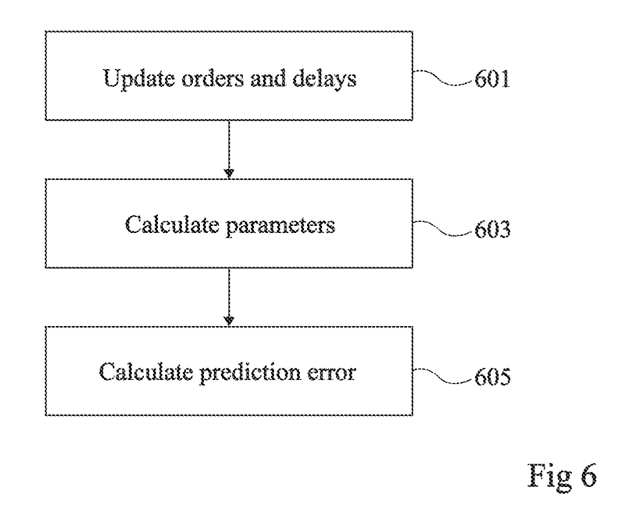
FIG. 6 is a diagram illustrating an example of a method of constructing the model of FIG. 5.

FIG. 6 is a diagram illustrating an example of a method of construction of the model of FIG. 5. More particularly, given the model structure described hereabove and defined by equation eq2, FIG. 6 illustrates an example of a model sizing method, that is, of determination of the orders $n_a$, $n_b$, $n_c$ and $n_d$ and of the delays $n_{k1}$, $n_{k2}$ and $n_{k3}$ of the model. To size the model, a database containing, for one or a plurality of patients, a history of the physical activity Pa(t) (for example, determined from a history of the output data of an accelerometer carried by the patient and from a patient's heart rate sensor), of the patient's carbohydrate intakes CHO(t), insulin intakes I(t), and real blood glucose (measured by a blood glucose sensor) $G^r(t)$ is here used.

The method of FIG. 6 comprises a step 601 during which a value is for example arbitrarily assigned to each of dimensions $n_a$, $n_b$, $n_c$, $n_d$, $n_{k1}$, $n_{k2}$ and $n_{k3}$ of the model.

The method of FIG. 6 then comprises a step 603 of calculation of the parameters of the model, that is, values $a_1, \ldots, a_{na}$, $b_1, \ldots, b_{nb}$, $c_1, \ldots, c_{nc}$, $d_1, \ldots, d_{nd}$. During this step, the patient's blood glucose is estimated based on the model over a past observation period, taking into account the history of insulin injection, of carbohydrate intake, and of physical activity, after which the curve G of the blood glucose estimated by the model is compared with the curve of real blood glucose $G^r$ measured by the sensor during this same period. A set of parameters $a_1, \ldots, a_{na}$, $b_1, \ldots, b_{nb}$, $c_1, \ldots, c_{nc}$, $d_1, \ldots, d_{nd}$ resulting in minimizing a quantity representative of the error between the curve of blood glucose estimated by the model and the real blood glucose curve during the observation period is then searched for. As an example, it is searched for a set of parameters leading to minimizing an indicator m representative of the area between the curve of the blood glucose estimated by the model and the curve of the real blood glucose measured by the sensor during the observation period, also called standard deviation between the estimated glucose and the real glucose, for example identical or similar to indicator m of the above-mentioned equation eq1. The optimal parameter search algorithm used during this step is not detailed in the present application, the described embodiments being compatible with usual algorithms used in various field to solve problems of parameter optimization by minimization of a cost function, for example, by the least squares method. It should be noted that in the case of a database comprising the history data of a plurality of patients, step 603 may comprise the successive steps of:

determination of a regression matrix for each patient based on the patient's history data;

concatenation of the regression matrices of the different patients; and determination of the optimal parameters of the model resulting in minimizing the error between the blood glucose curve estimated by the model and the real blood glucose curve.

The method of FIG. 6 further comprises, after step 603, once the optical parameters (for the dimensions determined at step 601) of the model have been determined, a step 605 of determination of the error between the blood glucose curve estimated by the model and the real blood glucose curve, over the considered past observation period. As an example, during this step, the error indicator calculated at step 603 for the considered set of parameters is stored.

The method of FIG. 6 is repeated a plurality of times by each time modifying one or a plurality of dimensions (order or delay) of the model. As an example, order $n_a$ is modified to successively take all the values of range [1,15], order $n_b$ is modified to successively take all the values of range [1,15], order $n_c$ is modified to successively take all the values of range [1,15], order $n_d$ is modified to successively take all the values of range [1,15], delay $n_{k1}$ is modified to successively take all the values of range [1,15], delay $n_{k2}$ is modified to successively take all the values of range [1,15], and delay $n_{k3}$ is modified to successively take all the values of range [1,15]. Thus, in the present example, the sequence of steps 601, 602, and 603 is repeated N=15*15*15*15*15*15=170859375 times.

At the end of the N iterations of the sequence of steps 601, 602, 603, the dimensions and the corresponding set of parameters resulting in the smallest error between the blood glucose curve estimated by the model and the real blood glucose curve, over the past observation period, are selected. As an example, the final dimensions of the model selected at the end of the method of FIG. 6 are the following: $n_a=3$, $n_b=5$, $n_c=11$, $n_d=7$, $n_{k1}=n_{k2}=n_{k3}=2$.

An advantage of the model of black box type described in relation with FIG. 5 is that it enables to perform particularly reliable predictions of the future trend of the patient's blood glucose, which is not allowed by known physiological models. Indeed, while it is well known that insulin favors the absorption of the glucose present in the blood by different organs of the body, and particularly by the muscles, and that the sensitivity to insulin and the absorption of the blood glucose by the muscles increase in the presence of a physical activity, the quantification of the combined effects of the different variables is very difficult to achieve. The use of a black box type model having as inputs the energy expenditure, the insulin on board, and the carbohydrate on board advantageously enables to obtain particularly reliable blood glucose predictions, particularly during and after a physical activity.

The prediction system of FIG. 4 may be used for many applications.

As an example, the system of FIG. 4 may be used to implement an MPC-type automated blood glucose regulation system such as described in relation with FIGS. 1 to 3, by replacing the physiological model 201 of FIG. 2 with the black box model 501 of FIG. 5.

As a variant, the prediction system of FIG. 4 may be used to implement an MPC-type automated blood glucose regulation system based on a physiological model, such as described in relation with FIGS. 1 to 3, the black box model 501 of FIG. 5 being used in redundancy with physiological model 201, to control the reliability of the predictions made based on the physiological model.

Figure 7:
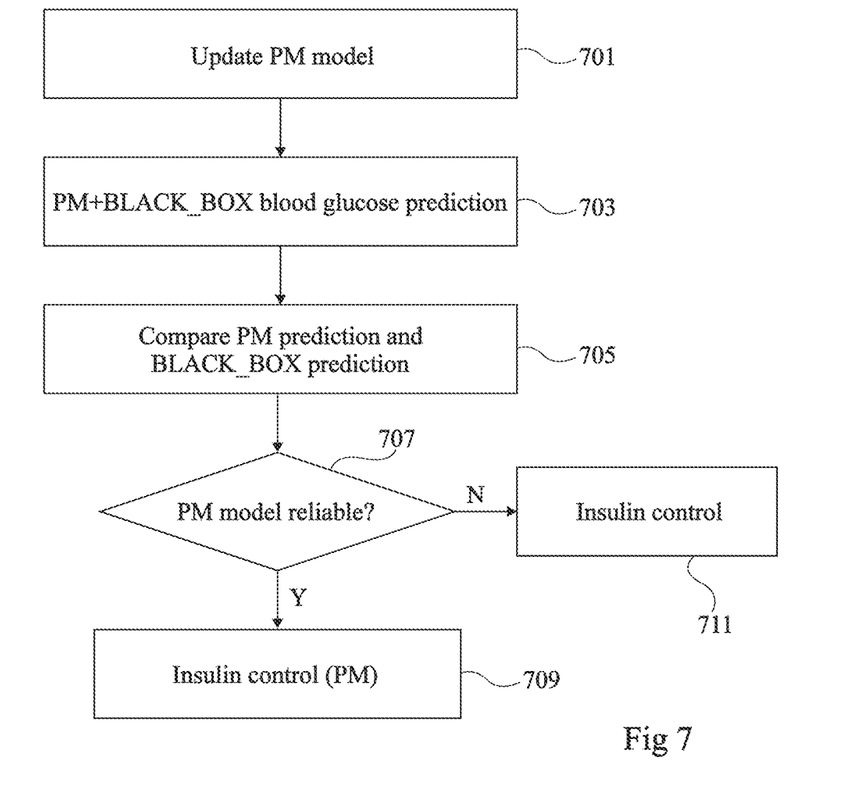
FIG. 7 is a diagram illustrating an example of an automated blood glucose control system capable of being implemented by the system of FIG. 4.

FIG. 7 is a diagram illustrating an example of an MPC-type automated blood glucose regulation system based on a physiological model, such as described in relation with FIGS. 1 to 3, where the black box model 501 of FIG. 5 is used to control the reliability of the predictions made based on the physiological model.

The method of FIG. 7 comprises a step 701 of recalibration or update of the physiological model identical or similar to step 301 of the method of FIG. 3. During this step, processing and control unit 401 implements a method of re-estimation of the time-dependent parameters of the model, taking into account the data relative to the insulin effectively injected by device 103 and the data relative to the real blood glucose measured by sensor 101 for a past observation period. More particularly, during the calibration step, processing and control unit 401 simulates the patient's behavior over the past observation period based on the physiological model (taking into account possible carbohydrate ingestions and insulin injections during this period) and compares the curve of the blood glucose estimated by the model with the curve of the real blood glucose measured by the sensor during this same period. Processing and control unit 401 then searches, for the time-dependent parameters of the model, a set of values leading to minimizing a quantity representative of the error between the blood glucose curve estimated by the model and the real blood glucose curve measured by the sensor during the observation period. During step 701, in addition to the time-dependent parameters of the physiological model, processing and control unit 401 may define a vector of initial states of the state variables of the model.

The method of FIG. 7 further comprises, after step 701, a step 703 of prediction, by processing and control unit 401, of the time variation of the patient's blood glucose over a prediction period to come of duration $T_{pred}$. During this step, two future blood glucose curves G1 and G2 are determined, the first one (curve G1) corresponding to the blood glucose prediction made based on the physiological model over the prediction period to come, identically or similarly to what has been described in relation with FIG. 3, and the second one (curve G2) corresponding to the blood glucose prediction made based on the black box model of FIG. 5 over the same prediction period to come.

The method of FIG. 7 further comprises, after step 703, a step 705 of comparison between the future blood glucose curve G1 estimated based on the physiological model and the future blood glucose curve G2 estimated based on the black box model. As an example, during this step, processing and control unit 401 calculates one or a plurality of numerical indicators representative of the deviation between the predicted blood glucose curves G1 and G2, for example, the mean standard deviation between the predicted blood glucose curves G1 and G2.

The method of FIG. 7 further comprises, after step 705, a step 707 of verification of the reliability of the physiological model updated at step 701. More particularly, during this step, the reliability of the physiological model is considered sufficient by processing and control unit 401 when the values of the indicators of the deviation between the future blood glucose curve G1 estimated based on the physiological model and the future blood glucose curve G2 estimated based on the black box model is (are) smaller than (a) predefined threshold(s), and insufficient in the opposite case.

If the physiological model is considered as sufficiently reliable at step 707 (O), a step 709 is implemented, during which processing and control unit 401 determines, taking into account the future blood glucose curve G1 estimated based on the physiological model, insulin doses to be injected to the patient during the prediction period to come. At the end of this step, processing and control unit 401 may program injection device 103 to deliver the determined doses during the prediction period to come.

If the physiological model is considered insufficiently reliable at step 707 (N), processing and control unit 401 stops using the physiological model to regulate the delivery of insulin to the patient and implements an alternative regulation method at a step 711. As an example, during step 711, processing and control unit 401 uses the future blood glucose curve G2 estimated based on the black box model of FIG. 5 to determine the insulin doses to be injected to the patient during the prediction period to come. As a variant, at step 711, processing and control unit 401 uses a simplified physiological model, for example, a compartmental model comprising a decreased number of state variables and number of parameters as compared with the initial model, to predict the trend of the patient's blood glucose and accordingly regulate the insulin injection. As a variant, at step 711, processing and control unit 401 stops implementing a predictive control, that is, it stops using a mathematical model to predict the patient's future blood glucose and accordingly regulate the insulin injection. In this case, processing and control unit 401 for example controls insulin injection device 103 to deliver pre-programmed insulin doses, for example corresponding to a reference basal rate prescribed to the patient. As a variant, processing and control unit 401 uses an algorithm of decisional matrix type to determine the insulin doses to be delivered to the patient, according to various observed parameters such as the current glucose level measured by sensor 101, or also the glucose variation speed (or slope) over a past period.

Steps 701, 703, 705, 707 and, possibly, 709 or 711, are for example periodically repeated, for example, every 1 to 20 minutes, and/or for each new carbohydrate ingestion notified by the patient, and/or for each new delivery of an insulin dose by injection device 103.

Figure 8:
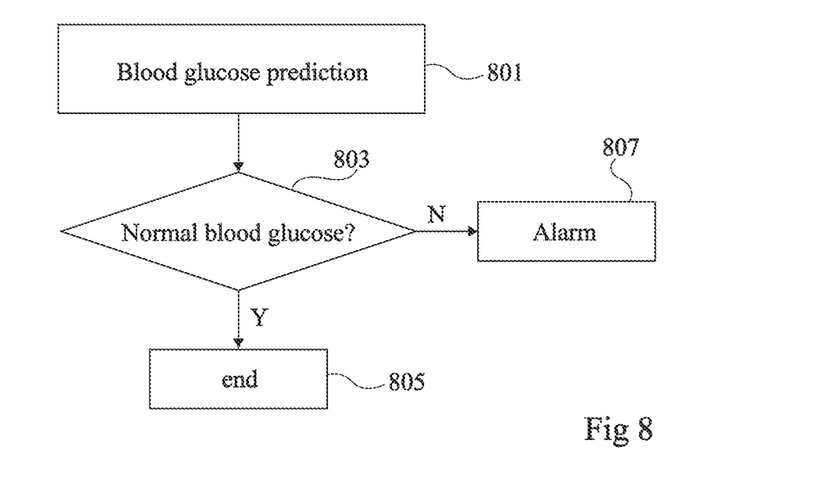
FIG. 8 is a diagram illustrating another example of an automated blood glucose control method capable of being implemented by the system of FIG. 4.

FIG. 8 is a diagram illustrating another example of an automated blood glucose control method capable of being implemented by the system of FIG. 4.

In this example, processing and control unit 401 may implement any blood glucose regulation method, for example, a closed loop regulation method of the type described in relation with FIGS. 1 to 3, or an open-loop regulation method where the patient him/herself defines the insulin doses to be injected based on his/her blood glucose rate, on his/her insulin injection history, and on his/her meal history.

In the example of FIG. 8, the black box model of FIG. 5 is used by processing and control unit 401 to predict the future trend of the patient's blood glucose, and trigger an alarm, for example, a sound and/or visual alarm, when the model predicts that the patient's blood glucose will come out of a desired range, for example, if there is a risk of hypoglycemia for the patient.

The method of FIG. 8 comprises a step 801 of prediction, by processing and control unit 401, based on the black box model of FIG. 5, of the time trend of the patient's blood glucose over a period to come.

The method of FIG. 8 further comprises, after step 801, a step 803 during which processing and control unit 401 determines whether the future blood glucose predicted by the model of FIG. 5 is or not a risk for the patient. For this purpose, processing and control unit 401 verifies that the future blood glucose curve predicted at step 801 does not come out of a desired range.

If, at step 803, the predicted blood glucose is deemed acceptable (O), the method ends at a step 805.

If, however, at step 803, the blood glucose is deemed unacceptable or dangerous for the patient (N), processing and control unit 401 triggers an alarm at a step 807, to warn the patient of the risk of hyperglycemia or of hypoglycemia, for example, to recommend him/her to stop any physical activity and/or to consume sugar in the case of a risk of hypoglycemia.

Steps 801, 803 and, possibly, 805 or 807, are for example periodically repeated.

Specific embodiments have been described. Various alterations, modifications, and improvements will occur to those skilled in the art. In particular, the described embodiments are not limited to the examples of use of the blood glucose prediction system of FIG. 4 described in relation with FIGS. 7 and 8. More generally, the provided prediction system, based on the use of the black box model of FIG. 5, may be used for any application capable of taking advantage of a reliable prediction of the future trend of a patient's blood glucose.

Further, the described embodiments are not limited to the above-described example where the input variable EE(t) of the model is calculated by taking into account an output signal of a sensor of the patient's movements and an output signal of a sensor of the patient's heart rate. As a variant, input variable EE(t) may be calculated by only taking into account the output signal of the motion sensor or only the output signal of the heart rate sensor. More generally, input variable EE(t) may be formed by any signal or combination of signals representative of the patient's physical activity. As an example, input variable EE(t) may be a combination of a signal measured by means of any sensor, for example, the motion sensor 405 and/or the heart rate sensor 407 of FIG. 4, and of a signal of physical activity intensity declared by the patient by means of a user interface (not detailed). As a variant, input variable EE(t) may be calculated only from a signal of activity intensity declared by the patient.

Further, the described embodiments are not limited to the specific case described hereabove where the black box model used to predict the patient's future blood glucose is an ARX-type model. More generally, any other type of black box model may be used, for example, an ARMAX-type model (Auto Regressive Moving Average with eXternal inputs), or a model based on a neural network.

Further, in addition to the above-described input variables EE(t), IOB(t), and COB(t), the model of FIG. 5 may comprise an additional input variable representative of the variability of the patient's heart rate, to take into account the stress in the blood glucose prediction made based on the model.

The invention claimed is:

1. An automated system for controlling a patient's blood glucose, comprising a processing and control unit configured to:
predict, based on a first mathematical model, a future trend of the patient's blood glucose over a prediction period, and
regulate, based on the prediction, insulin delivered to the patient, wherein the regulating comprises controlling an insulin injection device, wherein the first mathematical model takes as inputs:
a variable EE(t) representative of a time variation of the patient's energy expenditure;
a variable IOB(t) representative of a time variation of the patient's quantity of insulin on board; and
a variable COB(t) representative of a time variation of the patient's quantity of carbohydrate on board,
and wherein the first mathematical model is physiological model only defined by the observation of the effects of input variables EE(t), IOB(t) and COB(t) on the patient's blood glucose, without taking into account different known physiological mechanisms operating in the patient's body,
wherein, in operation, the processing and control unit receives a signal CHO(t), representative of a time variation of the quantity of carbohydrates ingested by the patient, and a signal I(t) representative of a time variation of the quantity of insulin injected to the patient, and wherein the processing and control unit is configured to calculate the input variables IOB(t) and COB(t) of the first mathematical model as follows:

$$IOB(t) = \Sigma_{k=0}^{K} I(t-k) * h_{IOB}(k) \text{ and}$$

$$COB(t) = \Sigma_{k=0}^{K} CHO(t-k) * h_{COB}(k),$$

where K is an integer greater than 1, k is an integer in the range from 0 to K, $h_{IOB}$ is an action function representing a time variation of an effect of the injected insulin on the absorption of blood glucose, and $h_{COB}$ is an action function representing a time variation of an effect of the ingested carbohydrates on the blood glucose.

2. The system according to claim 1, wherein the first mathematical model is defined as follows:

$$G(t) = a \cdot y_G + b \cdot u_{EE} + c \cdot u_{IOB} + d \cdot u_{COB},$$

where t is a discretized time variable, $a=[a_1, \ldots, a_{na}]$ is a vector of parameters of dimension $n_a$, $n_a$ being an integer greater than or equal to 1, $b=[b_1, \ldots b_{nb}]$ is a vector of parameters of dimension $n_b$, $n_b$ being an integer greater than or equal to 1, $c=[c_1, \ldots, c_{nc}]$ is a vector of parameters of dimension $n_c$, $n_c$ being an integer greater than or equal to 1, $d=[d_1, \ldots, d_{nd}]$ is a vector of parameters of dimension $n_d$, $n_d$ being an integer greater than or equal to 1, $y_G=[G(t-1), \ldots, G(t-n_a)]$ is a regression vector of dimension $n_a$, $u_{EE}=[EE(t-n_{k1}), \ldots, EE(t-n_{k1}-n_b)]$ is a regression vector of dimension $n_b$, $n_{k1}$ being an integer greater than or equal to 1, $u_{IOB}=[IOB(t-n_{k2}), \ldots, IOB(t-n_{k2}-n_c)]$ is a regression vector of dimension $n_c$, $n_{k2}$ being an integer greater than or equal to 1, and $u_{COB}=[COB(t-n_{k3}), \ldots, COB(t-n_{k3}-n_d)]$ is a regression vector of dimension $n_d$, $n_{k3}$ being an integer greater than or equal to 1.

3. The system according to claim 2, wherein $n_a$ is in range [1,15], $n_b$ is in range [1,15], $n_c$ is in range [1,15], $n_d$ is in range [1,15], $n_{k1}$ is in range [1,15], $n_{k2}$ is in range [1,15], and $n_{k3}$ is in range [1,15].

4. The system according to claim 1, wherein the action functions $h_{IOB}$ and $h_{COB}$ are defined as follows:

$$h_{IOB}(t) = \left[1 + \frac{t}{\tau_{IOB}}\right] e^{-\frac{t}{\tau_{IOB}}}, \text{ and}$$

$$h_{COB}(t) = \left[1 + \frac{t}{\tau_{COB}}\right] e^{-\frac{t}{\tau_{COB}}},$$

where $\tau_{IOB}$ and $\tau_{COB}$ are time constants.

5. The system according to claim 1, further comprising a device for measuring a patient's physical activity, the input variable EE(t) of the first mathematical model being calculated by the processing and control unit based on output data PA(t) of the device for measuring the patient's physical activity.

6. The system according to claim 5, wherein the device for measuring the patient's physical activity comprises a sensor of the patient's movements.

7. The system according to claim 6, wherein the device for measuring the patient's physical activity further comprises a sensor of the patient's heart rate.

8. The system according to claim 7, wherein the sensor of the patient's movements delivers a signal $S_{CPM}$ representative of movements performed by the patient, and the sensor of the patient's heart rate delivers a signal $S_{HR}$ representative of the patient's heart rate, and the input variable EE(t) of the first mathematical model is calculated as follows by the processing and control unit:

$$EE(t) = \begin{cases} \alpha_1 * S_{HR}(t) + \beta_1, & S_{HR} \geq S1 \\ \alpha_2 * S_{LC}(t) + \beta_2, & S_{HR} < S1 \text{ et } S_{LC} < S2, \\ \alpha_3 * S_{LC}(t) + \beta_3, & S_{HR} < S1 \text{ et } S_{LC} \geq S2 \end{cases}$$

where signal $S_{LC}$ is a linear combination of signals $S_{HR}$ and $S_{CPM}$, and quantities $\alpha_1, \alpha_2, \alpha_3, \beta_1, \beta_2, \beta_3$, S1, and S2 are parameters of the system, wherein $\alpha_1$ is a value between 1 and 10, $\alpha_2$ is a value between 100 and 500, $\alpha_3$ is a value between 10 and 200, $\beta_1$ is a value between −200 and 0, $\beta_2$ is a value between −10 and 10, $\beta_3$ is a value between 10 and 200, S1 is a value between 20 and 60, and S2 is a value between 0.1 and 1.

9. The system according to claim 1, wherein the processing and control unit is configured to predict, based on the first mathematical model, the future trend of the patient's blood glucose over a prediction period, to determine whether the blood glucose predicted by the first mathematical model remains or is not contained within a desired range, and to trigger an alarm if the blood glucose predicted by the first mathematical model comes out of the desired range.

10. The system according to claim 1, further comprising a blood glucose sensor and an insulin injection device, wherein the processing and control unit is capable of predicting the future trend of the patient's blood glucose based on a second mathematical model and of controlling the insulin injection device by taking the prediction into account, and the processing and control unit being configured to:

a) implement a step of automatic calibration of the second mathematical model by taking into account a history of the blood glucose measured by the sensor during a past observation period;

b) at the end of the calibration step, make a first prediction of the future trend of the patient's blood glucose based on the first mathematical model and, over the same prediction period, a second prediction of the future trend of the patient's blood glucose based on the second mathematical model;

c) calculate at least one numerical indicator representative of a deviation between the first and second predictions; and d) according to the value of the numerical indicator, control the insulin injection device by taking into account the second prediction or control the insulin injection device without taking into account the second prediction.

11. The system according to claim 10, wherein the second mathematical model is a physiological model comprising a differential equation system describing a time variation of a plurality of state variables.

12. The system according to claim 11, wherein step a) of automatic calibration of the second mathematical model comprises a step of estimation of parameters of the differential equation system by minimization of a quantity representative of the error, during the past observation period, between the blood glucose estimated based on the physiological model and the blood glucose measured by the sensor.

* * * * *

UNITED STATES PATENT AND TRADEMARK OFFICE
CERTIFICATE OF CORRECTION

| | | |
|---|---|---|
| PATENT NO. | : 11,883,162 B2 | Page 1 of 1 |
| APPLICATION NO. | : 16/982096 | |
| DATED | : January 30, 2024 | |
| INVENTOR(S) | : Hector-Manuel Romero Ugalde et al. | |

It is certified that error appears in the above-identified patent and that said Letters Patent is hereby corrected as shown below:

In the Claims

Column 16, Claim 1, Line 43 should read:
and wherein the first mathematical model is a non-physiological Column 17, Claim 4, Line 26 should read:
functions $h_{IOB}$ and $h_{COB}$ are defined as follows:

Signed and Sealed this
Twelfth Day of March, 2024

Katherine Kelly Vidal
*Director of the United States Patent and Trademark Office*